United States Patent [19]

King et al.

[11] Patent Number: 5,049,688

[45] Date of Patent: Sep. 17, 1991

[54] ALLYL CYCLOSILALACTAMS

[75] Inventors: Russell K. King; Chi-long Lee, both of Midland, Mich.

[73] Assignee: Dow Corning Corporation, Midland, Mich.

[21] Appl. No.: 661,564

[22] Filed: Feb. 15, 1991

[51] Int. Cl.$^5$ .............................................. C07F 7/10
[52] U.S. Cl. .................................................... 556/407
[58] Field of Search ......................................... 556/407

[56] References Cited

U.S. PATENT DOCUMENTS 3,803,194  4/1974  Golity et al. ........................ 556/407
4,680,410  7/1987  Wang .............................. 556/407 X
4,804,771  2/1989  Pepe .................................. 556/407

Primary Examiner—Paul F. Shaver
Attorney, Agent, or Firm—Roger H. Borrousch

[57] ABSTRACT

Cyclosilalactams of the formula

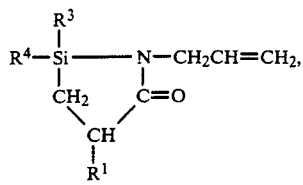

(A)

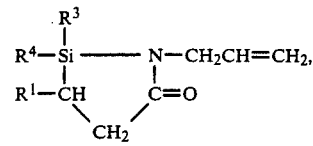

(B)

and

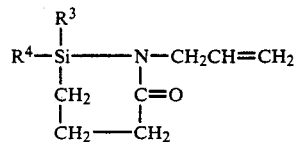

(C)

which can be used in the preparation of polyorganosiloxanes which react with moisture and do not have leaving groups. These cyclosilalactams are made using chlorosilabutanoic acid and chlorosilapropanoic acid precursors.

5 Claims, No Drawings

ALLYL CYCLOSILALACTAMS

BACKGROUND OF THE INVENTION

1. Field of the Invention

This invention relates to cyclosilalactams.

2. Background Information

A search for new crosslinkers for use in the preparation of room temperature vulcanizing silicones (RTV's) lead to the discovery of the cyclosilalactams of the present invention. Mironov et al in "Synthesis of Silalactams", Khim. Geterotsikl. Soedin. (Chemistry of Heterocyclic Compounds), 1968, Vol. 6, p. 1124 described the following silalactams of the general formula $$\begin{array}{c} CH_3 \\ | \\ CH_3-Si-N-R' \\ | \quad\quad | \\ CH_2 \quad C=O \\ | \quad\quad | \\ CH-(CH_2)_m \\ | \\ R \end{array}$$

where R and R' are hydrogen, methyl, ethyl, or propyl and m is 0 or 1. Compounds of general formula (I) are made by the following reactions $$\begin{array}{c} R \quad\quad O \quad CH_3 \\ | \quad\quad \| \quad | \\ CH_2=C-(CH_2)_m-C-O-Si-H + H_2PtCl_6 \longrightarrow \\ \quad\quad\quad\quad\quad\quad\quad | \\ \quad\quad\quad\quad\quad\quad\quad CH_3 \end{array}$$

$$[CH_2CH(CH_2)_m\overset{R}{\underset{|}{C}}-\overset{O}{\underset{\|}{}}\overset{CH_3}{\underset{|}{OSi}}]_x$$
$$\quad\quad\quad\quad\quad\quad\quad CH_3$$
(II)

where x is $\geq 2$.

$$(II) + SOCl_2 \longrightarrow ClSi(CH_3)(CH_3)CH_2CH(R)(CH_2)_mCCl(O) \;(III)$$

$$(III) + R'NH_2 \longrightarrow (I).$$

THE INVENTION

This invention relates to a compound which is a cyclosilalactam of general formula $$\begin{array}{c} R^3 \\ | \\ R^4-Si\text{———}N-CH_2CH=CH_2, \\ | \quad\quad\quad | \\ CH_2 \quad\quad C=O \\ \quad\backslash \quad\quad / \\ \quad\quad CH \\ \quad\quad | \\ \quad\quad R^1 \end{array}$$ (A)

$$\begin{array}{c} R^3 \\ | \\ R^4-Si\text{———}N-CH_2CH=CH_2, \\ | \quad\quad\quad\quad | \\ R^1-CH \quad\quad C=O \\ \quad\quad \backslash \quad / \\ \quad\quad CH_2 \end{array}$$ (B)

-continued
and $$\begin{array}{c} R^3 \\ | \\ R^4-Si\text{———}N-CH_2CH=CH_2 \\ | \quad\quad\quad | \\ CH_2 \quad\quad C=O \\ | \quad\quad\quad | \\ CH_2\text{———}CH_2 \end{array}$$ (C)

in which each of $R^1$, $R^3$, and $R^4$ is independently selected from the group consisting of a hydrogen atom and a monovalent hydrocarbon radical. The monovalent hydrocarbon radicals include methyl, ethyl, propyl, butyl, phenyl, vinyl, allyl, hexenyl, cyclohexyl, tolyl, and isopropyl. Preferably, $R^1$, $R^3$, or $R^4$ are methyl.

The cyclosilalactams of the present invention can be prepared by a method similar to the above method described by Mironov et al. However, the cyclosilalactams of the present invention of the present invention are prepared by the following methods.

The preparation of cyclosilalactam of formula (A) is made by first reacting a diorganosilyl ester of methacrylic acid having the formula $$\begin{array}{c} \quad\quad O \quad\quad R^3 \\ \quad\quad \| \quad\quad | \\ CH_2=C-C-O-Si-H \\ | \quad\quad\quad\quad\quad | \\ CH_3 \quad\quad\quad\quad R^4 \end{array}$$

with a platinum catalyst exemplified by chloroplatinic acid, complexes of chloroplatinic acid with sym-divinyltetramethyldisiloxane, and thionyl chloride ($SOCl_2$) with heating. The removal of the by-products which can be both solids and liquids produces a chlorosilylpropanoic acid precursor, namely 3chlorodiorganosilyl-2-methylpropanoic acid chloride of the formula $$\begin{array}{c} R^3 \quad\quad CH_3 \quad O \\ | \quad\quad\quad | \quad\quad \| \\ Cl-Si-CH_2CH-C-Cl \\ | \\ R^4 \end{array}$$

which is then reacted with allylamine producing a cyclosilalactam of formula (A).

The cyclosilalactams of formula (B) and (C) can be prepared by a method which produces both at the same time. A chlorosilane of the formula $$\begin{array}{c} R^3 \\ | \\ H-Si-Cl \\ | \\ R^4 \end{array}$$

is reacted with trimethylsilyl ester of vinylacetic acid in the presence of a platinum catalyst such as described above with heating. After the reaction, thionyl chloride is slowly added to the solution to give a mixture of chlorosilabutanoic acid chloride represented by the general formula $$\begin{array}{c} R^3 \quad R^2 \quad\quad O \\ | \quad\quad | \quad\quad \| \\ Cl-Si-CH(CH_2)_nC-Cl \\ | \\ R^4 \end{array}$$

where $R^2$ is a hydrogen atom or methyl radical and n is 1 or 2. The mixture of chlorosilylbutanoic acid chlorides preferably have the formulae

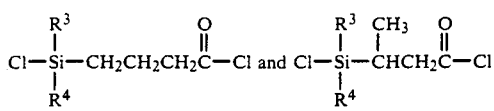

The addition of allylamine to the above mixture of chlorosilanes produces a mixture of cyclosilalactams of formula (B) and (C).

These cyclosilalactams are useful for making polyorganosiloxanes which have reactive endgroups in the presence of moisture and do not produce leaving groups upon reaction.

The following examples are presented for illustrative purposes and should not be construed as limiting the present invention which is properly delineated in the claims.

EXAMPLE 1

Synthesis of 1-Allyl-6,6-Dimethyl-6-Sila-2-Piperidone and 1-Allyl-4,5,5-Trimethyl-5-Sila-2-Pyrrolidone 112.5 Grams of dimethylchlorosilane was slowly added to a solution of 142.48 g (0.900 mol) of the trimethylsilyl ester of vinylacetic acid and 0.05 g of a chloroplatinic acid complex with sym-divinyltetramethyldisiloxane having a platinum content of about 0.7 weight percent in 140 g of toluene while heating between 90° C. to 120° C. After the addition, 129 g of thionyl chloride was slowly added at reflux. A small amount of yellowish precipitate formed. The toluene, excess thionyl chloride, and trimethylchlorosilane were distilled at reduced pressure. The product was distilled at 68° C. to 69° C. and 0.05 mmHg to yield 144 g (73%) of product, which was a mixture of 4-chlorodimethylsilylbutanoic acid chloride and 3-chlorodimethylsilylbutanoic acid chloride. 17.73 Grams of allylamine was slowly added with cooling and stirring to a solution of 22.27 g (0.1035 mol) of the mixture of above butanoic acid chlorides in diethyl ether. An extremely exothermic reaction occurred with the formation of solid allylammonium chloride which was removed by filtration. The ether was removed at room temperature under vacuum. The residue was distilled at 76° C. and 0.03 mmHg to yield 15.50 g (75.1%) of a 2:1 weight ratio of

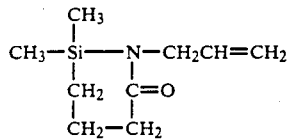
(C)

to

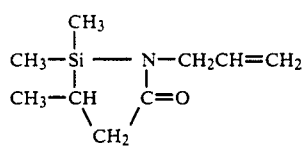
(B)

EXAMPLE 2

Preparation of 3-Chlorodimethylsilyl-2-Methylpropanoic Acid Chloride via Intramolecular Hydrosilation of Dimethylsilyl Ester of Methacrylic Acid and Synthesis of 1-Allyl-3,5,5-Trimethyl-5-Sila-2-Pyrrolidone 91.74 g (0.636 mol) of the dimethylsilyl ester of methacrylic acid was slowly added over a 1.5 hour period to a solution of 0.05 g of the platinum complex described in Example 1 in 60 ml of toluene at 110° C. After the addition, 90.8 g (0.763 mol) of thionyl chloride was slowly added over a 25 minute period to the solution at reflux. A considerable amount of black precipitate formed towards the end of the addition. The reaction was heated with stirring at 85° C. overnight. The brown liquid was decanted from the solids and the toluene and excess thionyl chloride were distilled at reduced pressure. The product was distilled at 71° C. to 73° C. and 0.05 mmHg to yield 98.5 g (72% yield) of lemon product identified as 3-chlorodimethylsilyl-2-methylpropanoic acid chloride.

1-Allyl-3,5,5-trimethyl-5-sila-2-pyrrolidone was prepared as follows: To a solution of 72.05 g (334.9 mmol) of 3-chlorodimethylsilyl-2-methylpropananoic acid chloride dissolved in 550 ml of diethyl ether was slowly added 63.10 g (1.105 mmol) of allyl amine with stirring over one hour. After stirring overnight, the solids were removed by filtration, and washed with two 100 ml portions of diethyl ether. The ether was removed from the combined organic phases and the product distilled at 140° C. and 0.05 mmHg. The yield was 60.88 g (91%) of the product had the following formula

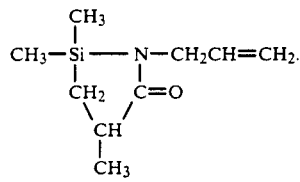

That which is claimed is:

1. A compound selected from the group consisting a cyclosilalactam of general formula

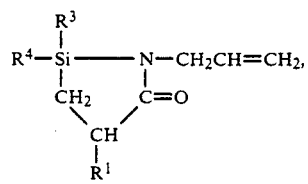
(A)

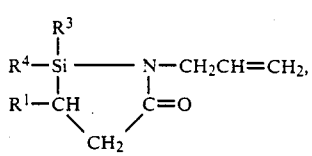
(B)

and

-continued

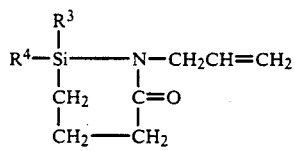
(C)

in which each of $R^1$, $R^3$, and $R^4$ is independently selected from the group consisting of a hydrogen atom and a monovalent hydrocarbon radical.

2. The compound according to claim 1 in which each $R^1$, $R^3$, and $R^4$ are methyl.

3. The compound according to claim 2 which is 1-allyl-6,6-dimethyl-6-sila-2-piperidone.

4. The compound according to claim 2 which is 1-allyl-4,5,5-trimethyl-5sila-2-pyrrolidone.

5. The compound according to claim 2 which is 1-allyl-3,5,5-trimethyl-5-sila-2-pyrrolidone.

* * * * *